Aug. 23, 1932. R. L. CATRON Plant Pat. 23
ROSE
Filed Jan. 16, 1932
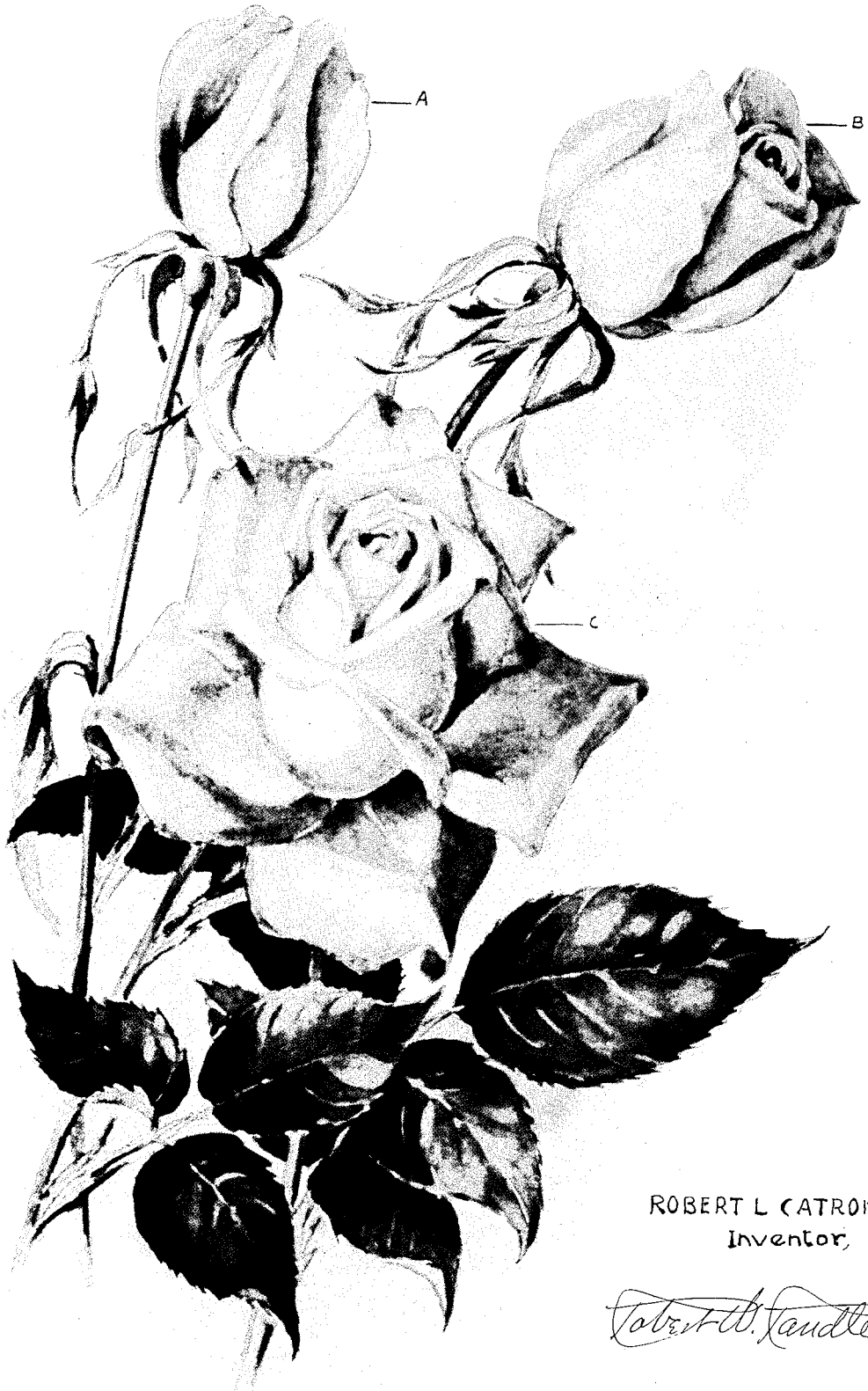
ROBERT L CATRON,
Inventor,
Robert H. Kandle,
Attorney.

Patented Aug. 23, 1932

Plant Pat. 23

UNITED STATES PATENT OFFICE

ROBERT LEE CATRON, OF RICHMOND, INDIANA, ASSIGNOR TO THE JOSEPH H. HILL COMPANY, OF RICHMOND, INDIANA, A CORPORATION OF INDIANA

ROSE

Application filed January 16, 1932. Serial No. 587,098.

Broadly stated, this invention relates to the production of a new and distinct variety of rose, which is unique in character, delectable in appearance, asexually produced, and whose characteristics are permanently fixed whereby it may be continuously reproduced without retrogradation.

More specifically stated, my present invention relates to a new and distinct variety of rose, the same being first naturally produced as a sport from a Briarcliff rose plant, then manually and asexually developed scientifically, whereby its characteristics have become fixed and its identity preserved and by which it will not retrograde to its progenerator by protracted asexual propagation, or otherwise.

Other objects and characteristics of my new rose will be more fully particularized in the following description, and the essential requisites thereof will be pointed out in the appended claim.

The accompanying illustration, forming a part of this specification, shows my new rose in its natural colors, wherein letter A denotes a virgin bud; letter B denotes a partly developed bud; and letter C denotes a full blown rose.

My new rose was produced from a sport originating from a Briarcliff rose plant. It was asexually reproduced whereby it will not revert.

My rose is similar to the Briarcliff rose, except as to the color of the bloom; also that it does not have so many small petals, but it has more large petals, which petals are usually thirty-six to fifty, in number, to each bloom. It also differs in that it is more fragrant than its progenitor; and in which the fragrance is of a more delicate and attractive nature. My rose is a brilliant cerise in color, with the fragrance thereof of unusually long duration, and in which the bloom is unusually prolific and of very large size.

My new rose was asexually produced as follows: A Briarcliff rose plant, which normally produces blooms which are light pink in color, voluntarily produced a sport bloom which was, in color, a brilliant cerise. The buds of said sport bloom were rebudded for a number of times and came back true to the original sport bloom, whereby the color, and other characteristics, of the original sport became fixed and may now be reproduced by grafting or budding or otherwise, without deterioration.

I desire that it be understood that considerable allowance is to be given in the production of my rose, as the size of the bloom, the brightness or brilliancy, the paleness, and the color shade thereof will vary somewhat, on account of differences in the soil, the amount of sunshine and moisture, its freedom from diseases, fungus, and insects, but such variations are but climatic or conditional.

The above described rose has been originated since the enactment of the Townsend-Purnell Plant Patent Act of 1930; and it has not been introduced to the public up to this date.

Having now fully shown and described my new rose, together with its origin, and the manner of its asexual production, what I claim and desire to secure by Letters Patent of the United States, is—

A rose substantially as shown and described, characterized by its bloom being brilliant cerise in color, having a delicate and attractive fragrance of long duration, and in which the petals are unusually prolific and of very large size.

In testimony whereof I have hereunto subscribed my name.

ROBERT LEE CATRON.